United States Patent [19]

Durrett et al.

[11] Patent Number: 4,977,377

[45] Date of Patent: Dec. 11, 1990

[54] MICROWAVE WATER CUT MONITOR WITH TEMPERATURE CONTROLLED TEST CELL

[75] Inventors: Michael G. Durrett; David A. Helms; Gregory J. Hatton, all of Houston; Earl L. Dowty, Katy; John D. Marrelli, Houston; Joseph D. Stafford, Bellaire; David J. Stavish, Houston, all of Tex.

[73] Assignee: Texaco Inc., White Plains, N.Y.

[21] Appl. No.: 337,709

[22] Filed: Apr. 13, 1989

[51] Int. Cl.$^5$ .............................................. G01N 22/00
[52] U.S. Cl. ................................ 324/640; 73/61.1 R; 324/606; 324/637; 324/647
[58] Field of Search .................... 324/58.5 A, 58.5 R, 324/58 A, 58 R, 441, 640, 641, 637, 606, 647, 639; 73/61.1 R

[56] References Cited

U.S. PATENT DOCUMENTS

| | | | |
|---|---|---|---|
| 4,240,028 | 12/1980 | Davis, Jr. | 324/61 R |
| 4,485,284 | 11/1984 | Pakulis | 324/58.5 A X |
| 4,490,676 | 12/1984 | Davis, Jr. et al. | 324/58.5 A X |
| 4,499,418 | 2/1985 | Helms et al. | 324/58.5 A |
| 4,651,085 | 3/1987 | Sakurai et al. | 324/58.5 R |
| 4,672,322 | 6/1987 | Gratteau et al. | 324/441 |
| 4,764,718 | 8/1988 | Reuns et al. | 324/58.5 A |
| 4,767,982 | 8/1988 | Florig et al. | 324/58.5 A |
| 4,774,680 | 9/1986 | Agar | 364/550 |
| 4,881,412 | 11/1989 | Northedge | 73/861.04 |

Primary Examiner—Reinhard J. Eisenzopf
Assistant Examiner—Robert W. Mueller
Attorney, Agent, or Firm—Robert A. Kulason; James J. O'Loughlin; Ronald G. Gillespie

[57] ABSTRACT

A petroleum stream microwave water cut monitor includes test cell means which contains a reference petroleum multiphase fluid sample and which has a sample stream of a petroleum stream passing through it. The test cell is maintained at a predetermined temperature. A source provides microwave energy to one of a first pair of antennae which provides the petroleum stream flowing in the test cell or the reference sample in the test cell with microwave energy. One of a second pair of antennae receives the microwave energy that has passed through either the petroleum stream or the reference sample. A detector detects the received microwave energy and provides a signal corresponding thereto. An indicator provides an indication of the water cut of the petroleum stream in accordance with the received signal power and a phase difference between the source provided microwave energy and the received microwave energy.

7 Claims, 2 Drawing Sheets

MICROWAVE WATER CUT MONITOR WITH TEMPERATURE CONTROLLED TEST CELL

BACKGROUND OF THE INVENTION

1. Field of the Invention

The present invention relates to water cut monitors in general and, more particularly, to microwave water cut monitors.

SUMMARY OF THE INVENTION

A petroleum stream microwave water cut monitor includes test cell means which contains a reference petroleum multiphase fluid sample and which has a sample stream of a petroleum stream passing through it. The test cell is maintained at a predetermined temperature. A source provides microwave energy to one of a first pair antennae which provides the petroleum stream flowing in the test cell or the reference sample in the test cell with microwave energy. One of a second pair of antennae receives the microwave energy that has passed through either the petroleum stream or the reference sample. A detector detects the received microwave energy and provides a signal corresponding thereto. An indicator provides an indication of the water cut of the petroleum stream in accordance with the received signal power and a phase difference between the source provided microwave energy and the received microwave energy.

The objects and advantages of the invention will appear more fully hereinafter from a consideration of the detailed description which follows, taken together with the accompanying drawing wherein one embodiment of the invention is illustrated by way of example. It is to be expressly understood, however, that the drawings are for illustration purposes only and are not to be construed as defining the limits of the invention.

DESCRIPTION OF THE INVENTION

Figure 1:
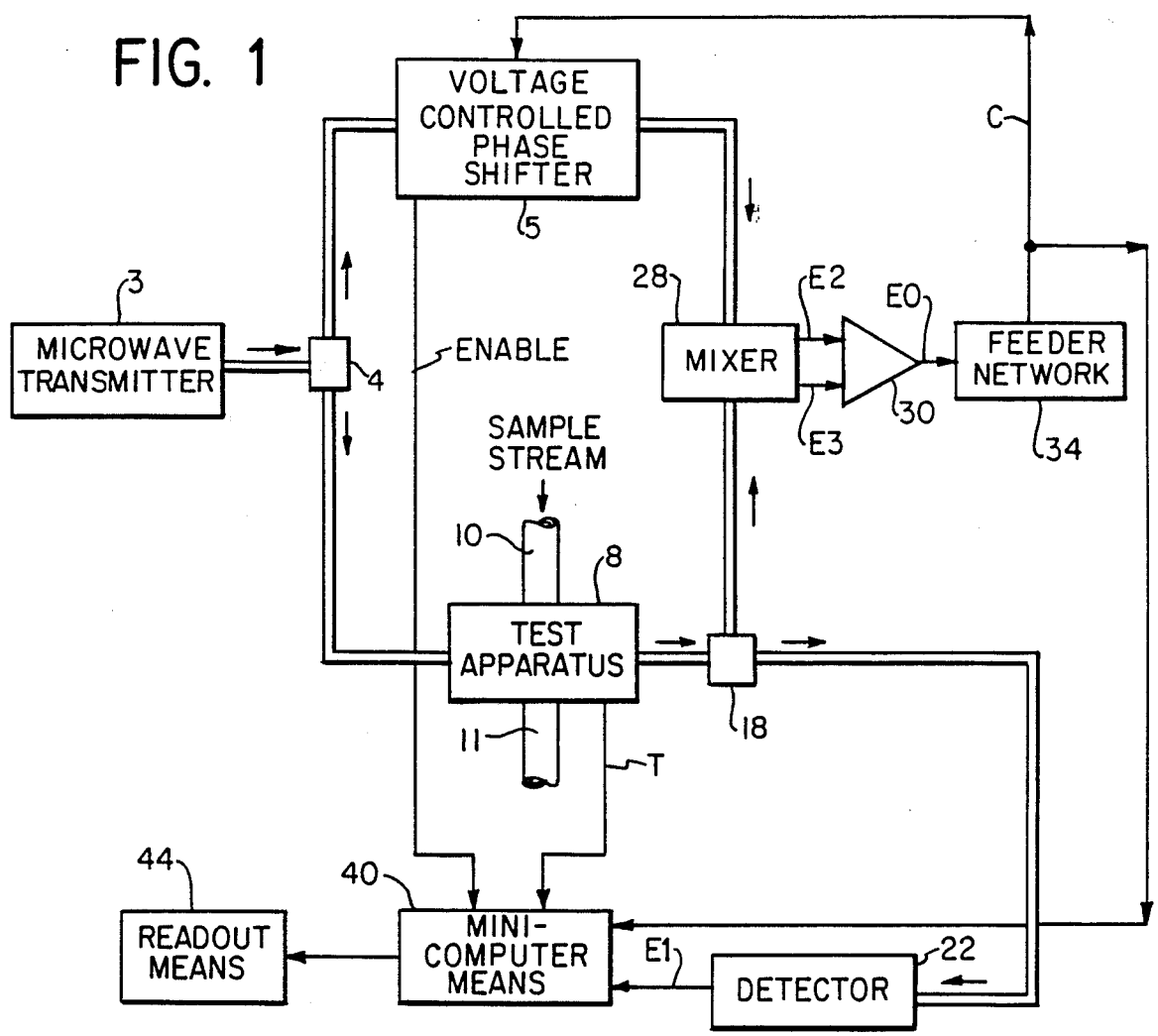
FIG. 1 is a partial simplified block diagram and a partial schematic of a microwave water cut monitor constructed in accordance with the present invention.

The water cut monitor shown in FIG. 1 includes a microwave transmitter 3 providing electromagnetic energy, hereinafter referred to as microwave energy, at a microwave frequency. Transmitter 3 is low powered and may use a microwave gun source. Transmitter 3 provides microwave energy to directional coupler 4. Directional coupler 4 provides microwave energy to a conventional type voltage controlled phase shifter 5 and to test apparatus 8. All conductance or carrying of microwave energy is accomplished by using conventional type waveguides and coaxial cables.

Test apparatus 8 has a line 10, carrying a sample stream of a multi-phase petroleum stream, entering apparatus 8. The sample stream leaves test apparatus 8 by way of a line 11. Apparatus 8 will be described in more detail hereinafter. Suffice to say at this point that microwave energy leaving test apparatus 8 in line 11, hereinafter referred to as test microwave energy, is microwave energy that is either passed through the sample stream or has passed through a reference sample. The test microwave energy is applied to a directional coupler 18. Directional coupler 18 provides the test microwave energy to a detector 22 and to a mixer 28. Detector 22 provides an intensity signal E1 corresponding to the power of the microwave energy received by antenna 16 or 70 and hence the intensity of the received microwave energy.

Voltage control phase shifter 5 provides microwave energy, hereinafter called the reference microwave energy, to mixer 28 which mixes the reference microwave energy and the test microwave energy to provide two electrical signals E2, E3, representative of the phases of the reference microwave energy and the test microwave energy, respectively.

A differential amplifier 30 provides an output signal E0 in accordance with the difference between signals E2 and E3. Signal E0 is a function of the phase difference between the reference microwave energy and the test microwave energy and is provided to a feedback network 34. Feedback network 34 provides a signal C to voltage control phase shifter 5, controlling the phase of the reference microwave energy, and to a mini-computer means 40. Signal E0, and hence signal C, decreases in amplitude until there is substantially 90° phase difference between the reference microwave energy and the test microwave energy. Voltage control phase shifter 5 indicates the amount of phase shift required to eliminate the phase difference.

Signals E1, T and C are provided to a conventional type mini-computer means 40 which contains within it memory means having data related to phase and power for various percentages of water cuts that could be encountered in the production stream. Phase Shifter 5 also provides an enable signal to computer means 40 allowing computer means 40 to utilize signals T, C and E1 as address signals to select the proper water cut value. Computer means 40 provides signals, corresponding to the selected water cut value, to readout means 44 which may be either display means or record means or a combination of the two.

Figure 2:
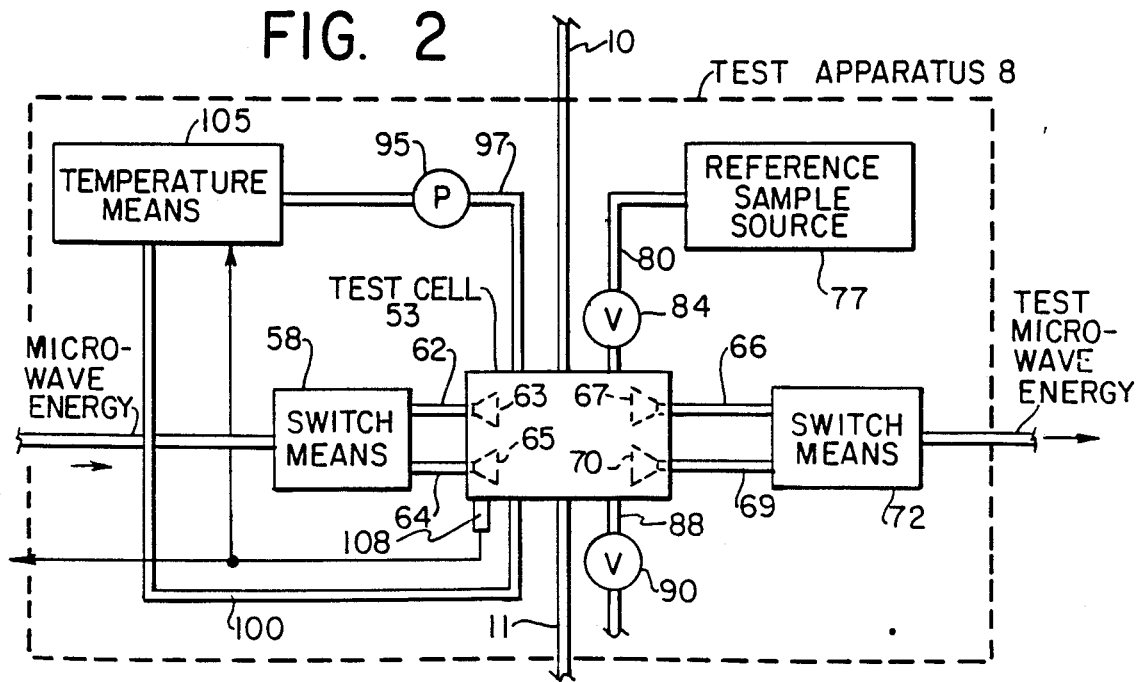
FIG. 2 is a simplified block diagram of the test apparatus shown in FIG. 1.

With reference to FIGS. 1 and 2, test apparatus 8 includes a test cell 53. Test cell 53 will be described more fully hereinafter. Microwave energy from directional coupler 4 enters switch means 58 which provides microwave to test cell 53 through either a line 62 or a line 64. Line 62 provides the microwave to an antenna 63 which radiates the microwave energy into the sample stream. Similarly, when microwave energy is provided by line 64, it is provided to an antenna 65. Antenna 65 radiates the microwave energy into the reference sample. Line 66 carries test microwave energy received by an antenna 67 after it has passed through the sample stream. Similarly, line 69 carries microwave energy received by an antenna 70 after it has passed through the reference sample. Switch means 72 receives the test microwave energy from either line 66 or line 67 and provides it to directional coupler 18.

A reference sample source 77 provides the reference sample fluid to test cell 53 by way of a line 80 having a valve 84. A channel in test cell 53 connects line 80 to another line 88 having a valve 90. In operation, source 77 provides the reference fluid through test cell 53. A measurement could be made while it is flowing, or sample fluid could be contained in a static condition in test cell 53 by closing valve 90 until the channel within test cell 53 is completely filled. To drain the reference sample fluid from test cell 53 valve 84 is closed while valve 90 is opened.

However, the temperature of the sample stream flowing through test cell 53 is important since variations in temperature will lead to different readings. The present invention controls the temperature of the sample stream flowing through test cell 53. In this regard a pump 95 pumps a fluid heated to a predetermined temperature through a line 97 to test cell 53 which leaves test cell 53 by way of line 100. The heating fluid is provided to a temperature control means 105 which heats it to the predetermined temperature and provides it to pump 95. Further, a temperature sensor 108 mounted in test cell 53, senses the temperature of test cell 53 and provides it back to temperature control means 105 so as to control the temperature of the heating fluid provided to pump 95.

Figure 3:
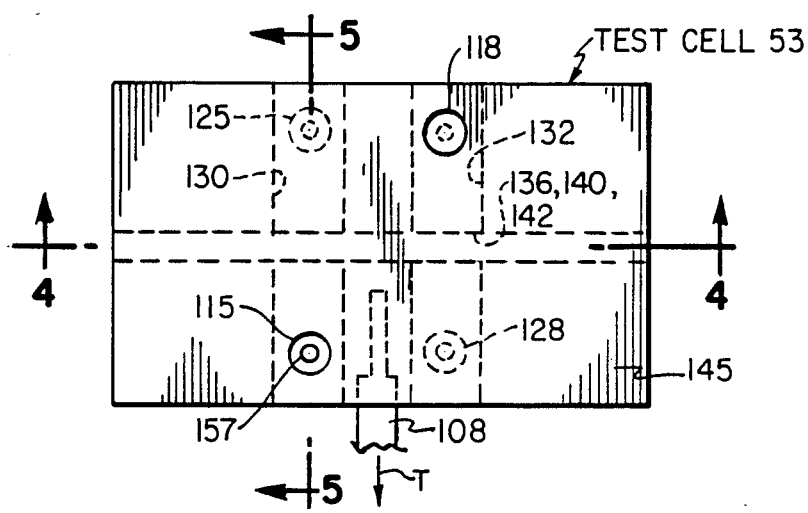
FIG. 3 is a drawing of the test cell shown in FIG. 2.

With reference to FIG. 3, there is shown test cell 53 having microwave entrance ports 115 and 118. On the other side of test cell 53 as represented by dash lines are microwave exit ports 125 and 128. Connecting microwave entrance port 115 and microwave exit port 125 is a microwave channel 130. Similarly a microwave channel 132 connects microwave entrance port 118 with microwave exit port 128.

Figure 4:
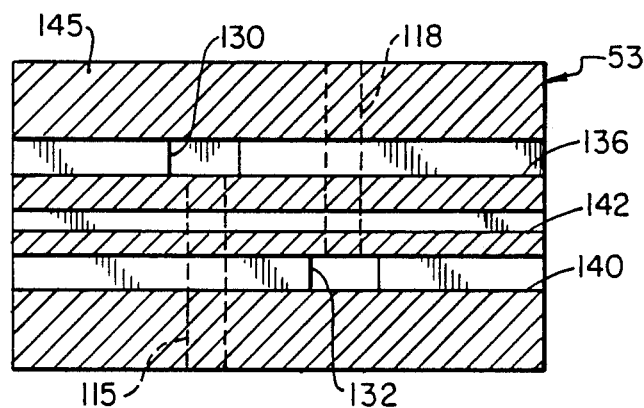
FIGS. 4 and 5 are cross-sectional drawings of the test cell shown in FIG. 3.

Also shown in FIG. 3 are fluid channels 136 and 140. Since fluid channels 136, 140 and 142 are in line in this View of test cell 53 only one set of dash lines represents them. This can seen better in FIG. 4 which has a cut away view of test cell 53 along the line 4—4 in the direction of the arrows. There is shown a body 145 which may be made of metal having fluid channels 136, 140 and 142 passing through it longitudinally and microwave channels 130 and 132 for the microwave energy cut transversely through it. It should be noted that channels 130 and 132 are shown as being offset from each other. However this offset is not necessary to the practice of the present invention.

It should also be noted that fluid channels 136, 140 have a rectangular cross-section so that the microwave energy that passes through the fluids, always has the same distance of passage.

Figure 5:
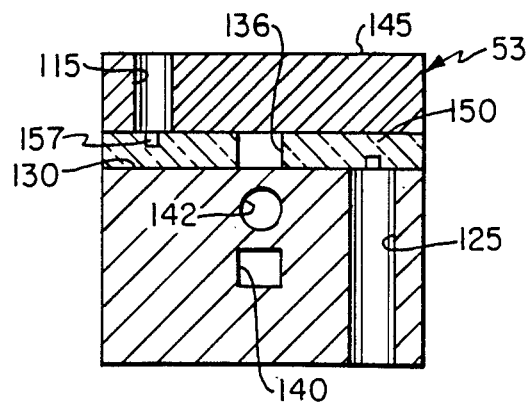

Referring to FIG. 5, there is a view of test cell 53 along the line 5—5 in the direction of shown in FIG. 3. Channel 130 is filled with a solid material 150, such as high density teflon, that is conductive to microwave energy, except for that portion of channel 130 that forms a cross-section of fluid channel 136. Cut into body 145 is microwave entrance port 115. Further there is another chamber 154 which connects microwave entrance port 111 and enters into material 150 in channel 130. This is for the insertion of microwave antenna 63, which may be of the commercial type made by Omni Spectra, Part No. 2057-5134-02. Similarly, microwave exit port 125, for antenna 67, is shown with an additional chamber 155 which enters into material 150. Again this is for the purpose of monitoring the sample stream. Basically it is the same type of antenna as is entered with entrance port 115, but again modified for the present application. As can be seen, exit port 125 is longer than entrance port 115. The microwave energy when applied to the antenna 63 enters material 150 and is directed to cross channel 136 until it reaches the antenna 67 inserted in exit port 125.

Referring also to FIG. 2, lines 10 and 11 are connected in a conventional manner to channel 136 so that the sample stream in line 10 will flow through test cell 53 to line 11. Similarly, lines 80 and 88 are connected to fluid channel 140 in such a manner that the sample fluid in line 80 will enter fluid channel 140 and exit test cell 53 through line 88. Similarly antenna 67 in entrance port 118 is connected to line 63 and antenna 70 in exit port 128 is connected to line 67.

As can be seen in FIG. 3, temperature sensor 108 which is a thermocouple, is inserted into a chamber cut into block 125 and thus reads the temperature of block 125 as the temperature of the reference sample and as of the production sample stream.

With reference also to FIGS. 2 and 3, lines 97 and 100 are connected in a conventional manner to fluid channel 142 so that the heating fluid flows through channel 142 and heats block 145. A preferred temperature is the temperature of the sample fluid entering test cell 53 from line 10 in which case it may be desirable to also test the temperature of the sample fluid in line 10 and provide a second temperature signal to the temperature control means. This has not shown in the drawings because the sample stream temperature may also be determined beforehand and is substantially constant. In either case the heating of block 125 will not add to the heat of the sample stream unless its temperature has changed. More important, however, the temperature of the sample stream as it passes through test cell 53 will be uniform. The reference sample will also be brought up to the temperature of the sample stream so that the data gathered from testing of both the sample stream and the reference sample will have a greater degree of accuracy.

Although channel 142 is shown as being located between fluid channels 136 and 140 if pressure is a problem and the strength of block 125 is suspect, fluid channel 142 may be moved with the idea in mind that it should generally be equidistant from the sample stream flowing in fluid channel 136 and the reference sample in fluid channel 140 so as to keep them at the same temperature.

Basically, the reference sample's power and phase shift is used as base line data in mini-computer means 40. The base line data and the test data derived from the petroleum sample stream are temperature corrected by mini-computer means 40. Mini-computer means 40 determines the water-cut in accordance with the corrected base line data, the corrected test data and look-up table stored in its memory.

What is claimed is:

1. A petroleum stream microwave water cut monitor comprising:

test cell means for containing a reference petroleum multiphase fluid sample and for having a sample stream of a petroleum stream flowing through it, temperature means connected to the test cell means for maintaining the test cell means at a predetermined temperature, source means for providing microwave energy, first antenna means connected to the source means for providing microwave energy into the petroleum sample stream or the reference sample, second antenna means for receiving microwave energy that has passed through the petroleum sample stream or the reference sample and providing the received microwave energy as test microwave energy, detector means connected to the second antenna means for detecting the power of the test microwave energy and providing a power signal corresponding thereto, and indicator means connected to the second antenna means, to the source means and to the detector means for providing an indication of the water cut of the petroleum stream in accordance with the power signal and the phase difference between the source provided microwave energy and the received microwave energy; and in which the test cell means includes:

a body having at least three channels therein for fluid passage and two channels for microwave energy passage, fluid source means for providing the reference sample to a first fluid channel, sample stream receiving means for receiving the sample stream and providing it to a second fluid channel, temperature control fluid receiving means for receiving the temperature control fluid and providing it to a third fluid channel, means for allowing the sample stream and the temperature control fluid to exit from the body; and wherein one fluid channel and one microwave channel intersect each other at right angles and the second fluid channel and the other microwave channel intersect each other at right angles.

2. A monitor as described in claim 1 in which the indicator means provides the indication of the water curtain accordance with the power signal, the phase difference between the source provided energy and the received microwave energy and the temperature signal.

3. A monitor as described in claim 2 in which the temperature means includes:

heat exchanger means connected to the test cell means for providing a temperature control fluid to and through the test cell means so as to maintain the test cell means at the predetermined temperature.

4. A monitor as described in claim 2 in which the temperature means further includes:

means connected to the heat exchange means and to the test cell means for returning the temperature control fluid from the test cell means back to the heat exchange means, temperature sensing means connected to the heat exchange means for sensing the temperature of the test cell means and providing a corresponding temperature signla to the heat exchange means, and in which the heat exchange means includes:

means connected to the temperature sensing means and responsive to the temperature signal for regulating the temperature of the temperature control fluid.

5. A monitor as described in claim 4 in which each microwave channel contains a material, except for that portion of the microwave channel that crosses a fluid channel, that is impervious to fluids but permits passage of the microwave energy.

6. A monitor as described in claim 5 in which the first antenna means includes:

first providing antenna means spatially arranged with one of the microwave channels for providing microwave energy into the one microwave channel, second providing antenna means spatially arranged with the other microwave channel for providing microwave energy into the other microwave channel, and first switch means connected to the source means and to the first and second transmitter antennas for providing the microwave energy transmitted by the source means to either the first transmitter antenna means or to the second transmitter antenna means; and the second antenna means includes:

a first receiving antenna spatially arranged with the one microwave channel, a second receiving antenna spatially arranged with the other microwave channel, second switching means connected to the first and second receiving antenna and cooperating with the first switching means for passing microwave energy that has passed through a fluid and received by a receiving antenna to the detector means and to the indicator means.

7. A monitor as described in claim 6 in which the solid material in the microwave channel is teflon.

* * * * *